United States Patent
McMorrow et al.

(10) Patent No.: US 6,884,217 B2
(45) Date of Patent: Apr. 26, 2005

(54) SYSTEM FOR AIMING ULTRASONIC BLADDER INSTRUMENTS

(75) Inventors: Gerald J. McMorrow, Duvall, WA (US); William Barnard, Kirkland, WA (US)

(73) Assignee: Diagnostic Ultrasound Corporation, Bothell, WA (US)

( * ) Notice: Subject to any disclaimer, the term of this patent is extended or adjusted under 35 U.S.C. 154(b) by 139 days.

(21) Appl. No.: 10/607,919

(22) Filed: Jun. 27, 2003

(65) Prior Publication Data

US 2004/0267123 A1 Dec. 30, 2004

(51) Int. Cl.[7] .............................................. A61B 8/00
(52) U.S. Cl. ...................................................... 600/443
(58) Field of Search ................................ 600/437–472; 128/916; 73/625, 626; 367/7, 11, 130, 138

(56) References Cited

U.S. PATENT DOCUMENTS

| | | | | |
|---|---|---|---|---|
| 4,926,871 A | * | 5/1990 | Ganguly et al. ............. | 600/443 |
| 5,159,931 A | * | 11/1992 | Pini ............................ | 600/443 |
| 5,235,985 A | * | 8/1993 | McMorrow et al. ......... | 600/443 |
| 5,381,794 A | * | 1/1995 | Tei et al. ..................... | 600/459 |
| 6,406,431 B1 | * | 6/2002 | Barnard et al. ............. | 600/443 |
| 2003/0216646 A1 | * | 11/2003 | Angelsen et al. ........... | 600/437 |

* cited by examiner

*Primary Examiner*—Ali Imam
(74) *Attorney, Agent, or Firm*—Jensen & Puntigam, P.S.

(57) ABSTRACT

The system includes a function for generating a plurality of ultrasound scan planes, each separated by a selected angle, to produce a scan cone having an ultrasound scan cone boundary for scanning the bladder, or other organ. The amount, if any, of the scanned bladder which extends beyond the ultrasound scan cone boundary is then determined, as well as the percentage of the bladder within an inner cone boundary relative to that within the ultrasound cone boundary. A signal is provided, specifically illumination of one of four orthogonal arrows in a display, indicating the direction that the transducer should be moved in order to more accurately center the bladder within the ultrasound scan cone boundary. Re-aiming of the transducer is considered necessary when the ratio of the percentages is less than 70%, while if the percentage ratio is greater than 70%, aiming is optional.

25 Claims, 3 Drawing Sheets

2D PHI MOTION

3D THETA MOTION

VIOLATION AREA ≈ BW-FW

SYSTEM FOR AIMING ULTRASONIC BLADDER INSTRUMENTS

TECHNICAL FIELD

This invention relates generally to ultrasonic bladder volume instruments, and more specifically concerns systems and methods for aiming such an instrument when it is positioned on the body, in order that an accurate ultrasound image of the bladder is obtained by the bladder instrument.

BACKGROUND OF THE INVENTION

Various apparatus using ultrasound technology to non-invasively measure the amount of urine in the human bladder are well known. Some examples of such apparatus are shown and described in U.S. Pat. Nos. 4,926,871; 5,235,985; 6,110,111 and 6,406,431, all owned by the assignee of the present invention. With each of those devices, a three-dimensional ultrasonic "field" is produced within which the bladder is captured and imaged. The accurate imaging of the entire bladder, however, requires that the instrument be accurately aimed toward the bladder on the body of a patient when the imaging is initiated.

In one example of a useful aiming method/system, a circle is depicted on an instrument display, which represents the field covered by the ultrasound cone. Typically, the displayed circle will include cross hairs. An outline of the bladder determined by the apparatus is then superimposed in the circle. The operator then moves the instrument around on the body of the user to center the bladder image as much as possible on the cross hairs. At that point, the determination of bladder volume is made from the ultrasound information.

While such a system works, there are some disadvantages. These include the requirement of a graphical LCD (liquid crystal display) on the apparatus, which increases the cost, complexity and power requirements of the apparatus. In addition, there are occasional operator errors or confusion relative to interpreting the image and determining when the image is sufficiently centered for an accurate scan, or which way the instrument must be moved to produce a proper aiming position.

Further, the three-dimensional ultrasound scans used for the aiming image typically require a relatively long time to acquire and display. The updating of the aiming display following adjustment of the position of the apparatus may not be as fast as is desirable in a typical patient setting, and may in addition cause some confusion on the part of the operator as to the actual result of previously moving the transducer.

Accordingly, the systems/methods disclosed herein are designed to overcome or decrease the above disadvantages of current systems.

SUMMARY OF THE INVENTION

Accordingly, the present invention is a system for aiming a transducer portion of an ultrasonic instrument in order to capture an image of a human organ, comprising: a function for generating a plurality of ultrasound scan planes, each scan plane being separated by a selected angle, to produce a scan cone having an ultrasound scan cone boundary for scanning a human organ, such as a bladder; a function for determining the amount, if any, of the scanned organ which extends beyond the cone boundary, defining a cone violation; a function for determining the extent to which the organ is centered within the ultrasound scan cone boundary when a cone violation is determined; and a signal display indicating that re-aiming of the ultrasound transducer is necessary when there is a cone violation and the organ is not centered by a selected amount.

BEST MODE FOR CARRYING OUT THE INVENTION

As indicated above, the present invention comprises several methods/systems for aiming, i.e. initially orienting, an ultrasonic transducer portion of a bladder instrument on the body of a patient, so as to capture as much as possible of the bladder within the three-dimensional field of view of the ultrasound scan.

Figure 1A:
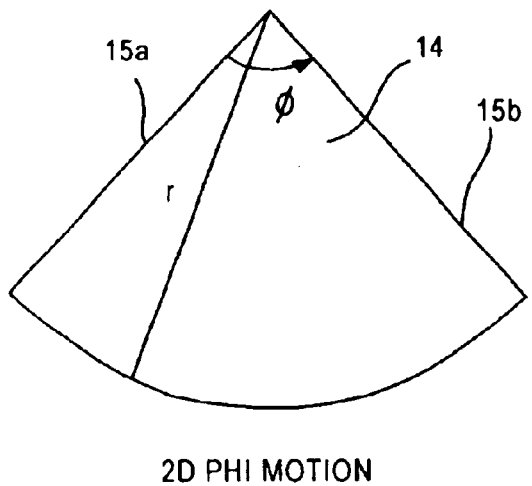
FIGS. 1A and 1B show one approach for generating an ultrasound cone in three-dimensional space for a bladder instrument.
Figure 1B:
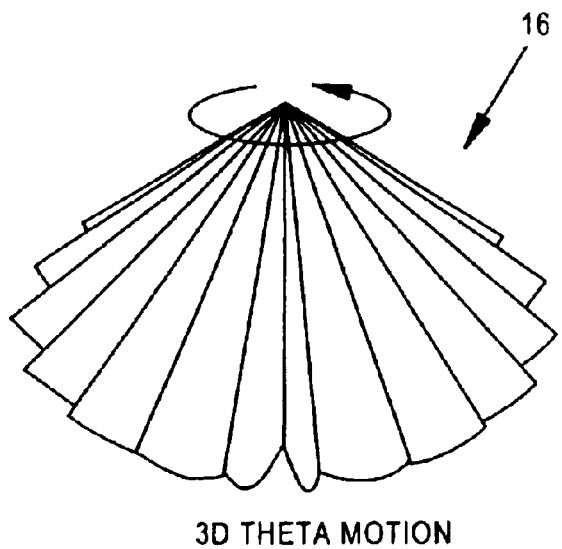

In one example of such a bladder instrument, ultrasound signals are used to sample a three-dimensional, solid angle scan cone. Such an instrument might, for instance, contain two stepper motors that move the transducer through three-dimensional space. Referring to FIGS. 1A and 1B, one motor in the apparatus moves the transducer in the phi ($\phi$) dimension in a single scan plane 14, also referred to as a scan line. Each scan plane spatially samples a segment of the complete ultrasound cone. The included angle of the scan plane (the angle between the two boundary edges 15a and 15b) can vary, but typically will be approximately 120°. The second transducer motor turns the transducer assembly about a central vertical axis through a total angle theta ($\theta$) in a series of small angular movements, as shown. Typically, the three-dimensional scan will cover an entire cone 16; hence, theta will be 360°, as shown in FIG. 1B.

In a typical arrangement, the assembly will rotate successively 7.5° in the theta direction; at each theta position an ultrasonic signal scan line, along a scan plane, is generated by the ultrasonic transducer. The total number of scan planes (lines) over the entire theta dimension of 360° will completely sample the imaged cone by ultrasonic signals. The ultrasound scan planes, specifically the boundaries thereof, define the boundaries of the imaged cone. The data, which is obtained from the ultrasound signals, is then processed to determine the bladder wall locations; this data is sometimes referred to as segmented data.

The present invention is for aiming or orienting the bladder scanning apparatus, in particular the transducer portion thereof, so that the ultrasound scan cone produced by the transducer captures within its boundaries the complete bladder of the patient or as much thereof as possible.

In use, the operator will initially position the transducer on the abdomen of the patient, with the patient in a supine position. The transducer at that point may or may not be appropriately aimed, i.e. it is uncertain as to whether or not the transducer is properly positioned to obtain an accurate three-dimensional ultrasound image, appropriate for bladder volume determinations. In one embodiment of the present invention, after the transducer has been initially positioned on the abdomen of the user, an ultrasound scan is made, and a determination is made as to whether or not any portion of the imaged bladder 11 extends beyond the ultrasound cone boundary 12 (see FIG. 3). If so, this is indicated to be a "cone violation".

An "outer cone" boundary 13 is defined to be slightly inside of the ultrasound cone boundary. In the embodiment shown, the included angle of the individual scan planes defining the cone is 120° while the "outer cone" boundary has an included angle of 116°, i.e. slightly smaller than the actual ultrasound scan cone included angle. These values can vary although the outer cone angle will always be less than the ultrasound cone boundary 12. In the embodiment shown, it is the outer cone boundary 13 which is used to make a more robust cone violation determination.

Figure 2:
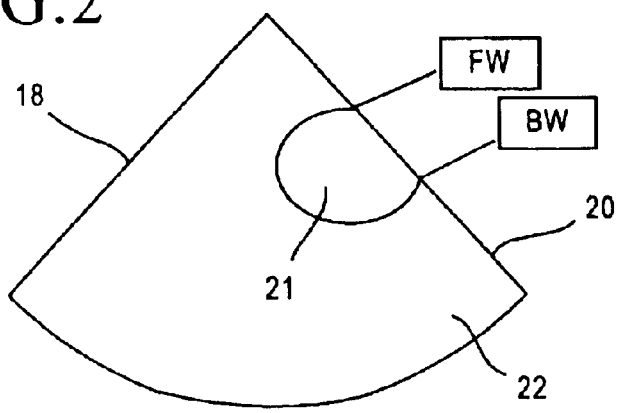
FIG. 2 shows a diagram of a single scan plane in an ultrasonic three-dimensional scan when the position of the bladder is such that it intersects one boundary edge of said scan line.

If a cone violation is determined, then the one particular scan plane which has the greatest cone violation is determined and the extent or amount of the cone violation in that scan plane is determined. In this embodiment, the distance between the front wall and the back wall of the bladder as it impinges on the scan line is used to determine the scan line with the greatest violation. This is shown in FIG. 2, where boundaries 18 and 20 of a single scan plane 22 are shown with a section 21 of the bladder being inside the area of the scan plane 22 and the remainder outside of the scan plane.

The area of violation relative to each scan line is determined by measuring the distance between the front wall and back wall intersections with the scan line by the bladder. This calculation is accomplished for each scan line, until the particular scan line having the greatest boundary violation is determined. It is at this point where the bladder extends beyond the outer scan cone the greatest distance. The total number of scan line boundaries which are exceeded by the bladder is also determined, in addition to the scan line having the greatest violation.

Figure 3:
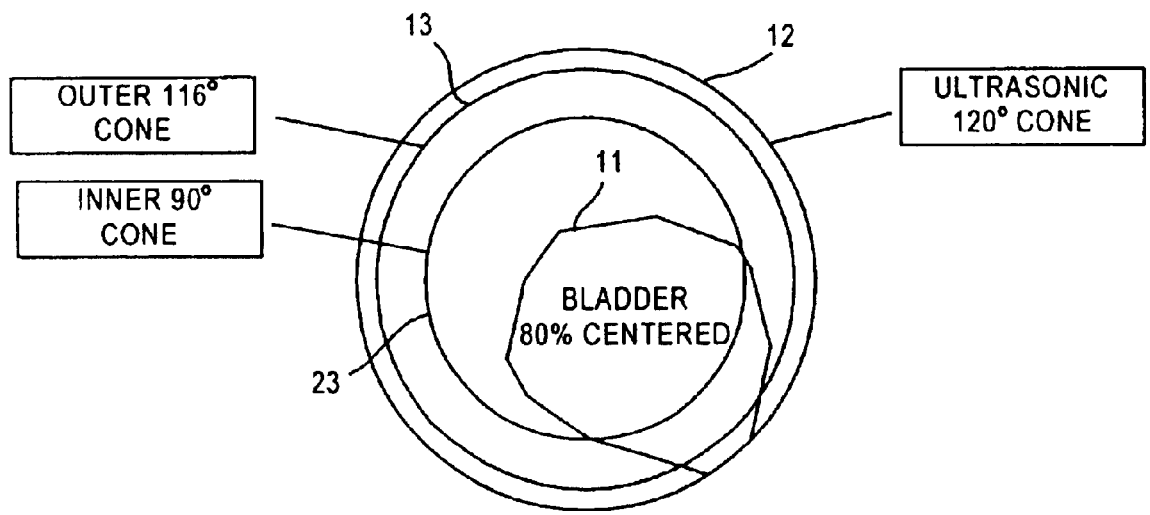
FIG. 3 illustrates one aiming system of the present invention.

The same above steps are accomplished for a cone of smaller included angle, which is referred to as an inner cone 23, shown in FIG. 3. In the embodiment shown, inner cone 23 has a 90° included angle, although this also can be varied.

Figure 4:
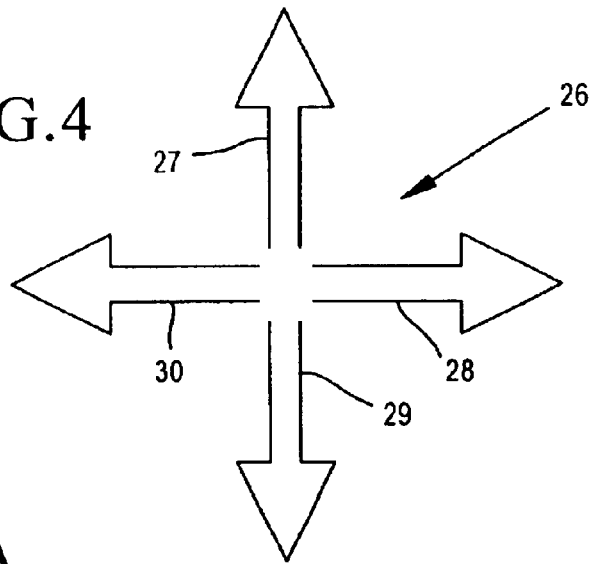
FIG. 4 is an aiming arrow display used in the embodiment of FIG. 3.

A percentage value or ratio is then determined of the number of scan planes for the inner cone not violated by the bladder position over the number of scan planes for the outer cone (or the ultrasound cone if there is no outer cone) not violated by the bladder, i.e. the amount of the bladder outside the inner cone over the amount of the bladder outside the ultrasound cone. The above percentage value information and the information concerning whether or not there has been any cone violation, are then used to light one of four orthogonal directional arrows, such as shown in FIG. 4. The orthogonal directional arrow display provides information to the operators as to which way (up, down or either side) to move the transducer on the patient. In the event that there is no cone violation of the outer cone or the ultrasonic cone, depending upon the embodiment, then none of the individual arrows in the display is lit, which indicates to the user that the device is properly aimed/oriented. At that point, the actual scanning of the bladder and determination of bladder volume can begin.

On the other hand, if there is a violation, then the one arrow in the display 26 is lit, which indicates the direction that the transducer should be moved to properly center (aim) the transducer. The percentage value (discussed above) is used to indicate whether or not the aim needs to be adjusted or whether the aim can be accepted at the operator's discretion.

In this embodiment, the percentage (ratio) threshold is 70%. This, however, can also be varied. In the embodiment shown, if there is a cone violation and the ratio is greater than 70%, then the directional arrow will be lit solid, which indicates that it is the operator's option to re-aim the device and produce another scan. On the other hand if the percentage is less than 70%, then the arrow blinks, indicating that the transducer must be re-aimed.

In this embodiment, there are four orthogonal arrows 27–30 in display 26 showing the four directions of movement of the device to center the bladder if a cone violation is detected. As indicated above, the lit "state" of the arrows provides an indication to the operator whether re-aiming is definitely necessary or optional. The two different lighting states can be varied as long as there is a difference between the two conditions which is known to the operator. The percentage threshold can also be different than 70%, although this value has proven to provide good results.

In a second embodiment, the transducer is arranged such that an initial operation of the instrument, after it has been initially positioned on the patient, such as by pushing a scan button or switch, produces a single scan plane. This embodiment improves (decreases) the time for the aiming function. Generally, ultrasonic scanners process the ultrasonic information for each scan plane in series, which, as the number of scan planes increase in order to increase resolution of the image, results in increasing scan acquisition and processing time to produce an image. Serial processing is required even with electronically steered transducers. In modern bladder volume instruments, 6–10 seconds of scan acquisition time is typically required.

Figure 5A:
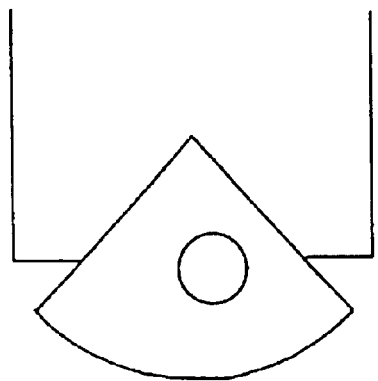
FIGS. 5A and 5B are ultrasound scans of the bladder.
Figure 5B:
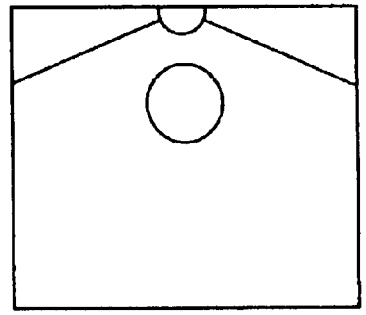

In the second embodiment, as indicated above, ultrasonic signals in a single scan plane, i.e. in a single "theta" plane, are produced when the scan switch or button on the instrument is operated. The single scan plane is generated continuously and a cross-section of the bladder from the single scan plane is determined. The display can either be an actual ultrasound display, such as shown in FIG. 5B, or a graphical machine-generated display from the ultrasound information, as shown in FIG. 5A.

In operation, the operator orients the transducer on the patient's abdomen in such a manner that the single continuously scanned "theta" plane is approximately parallel with the patient's mid-line. In this orientation, the ultrasonic field of view of the transducer will typically include the pubic bone, which in most cases tends to hide a portion of the bladder. The pubic bone has the effect of shadowing the bladder and results in a lower-than-true bladder volume reading. If any part of the cross-section of the bladder is blocked, as indicated by the display, however, the transducer can be moved/reoriented such that the pubic bone shadowing is minimized and as much as possible of bladder "seen" ultrasonically.

To achieve the desired results, the operator adjusts the angle of the transducer on the abdomen and/or applies pressure to one end of the transducer (elevating the other end) on the abdomen, attempting to maximize the cross-sectional area of the bladder on the display. The device can also be tilted, moved side to side or backward/forward or positioned at an angle, in order to provide this maximum cross-section. When a maximum cross-sectional area is determined, the scan button on the instrument is released and the transducer held in that physical position/orientation, while the follow-on entire three-dimensional cone information is generated and acquired.

Figure 6:
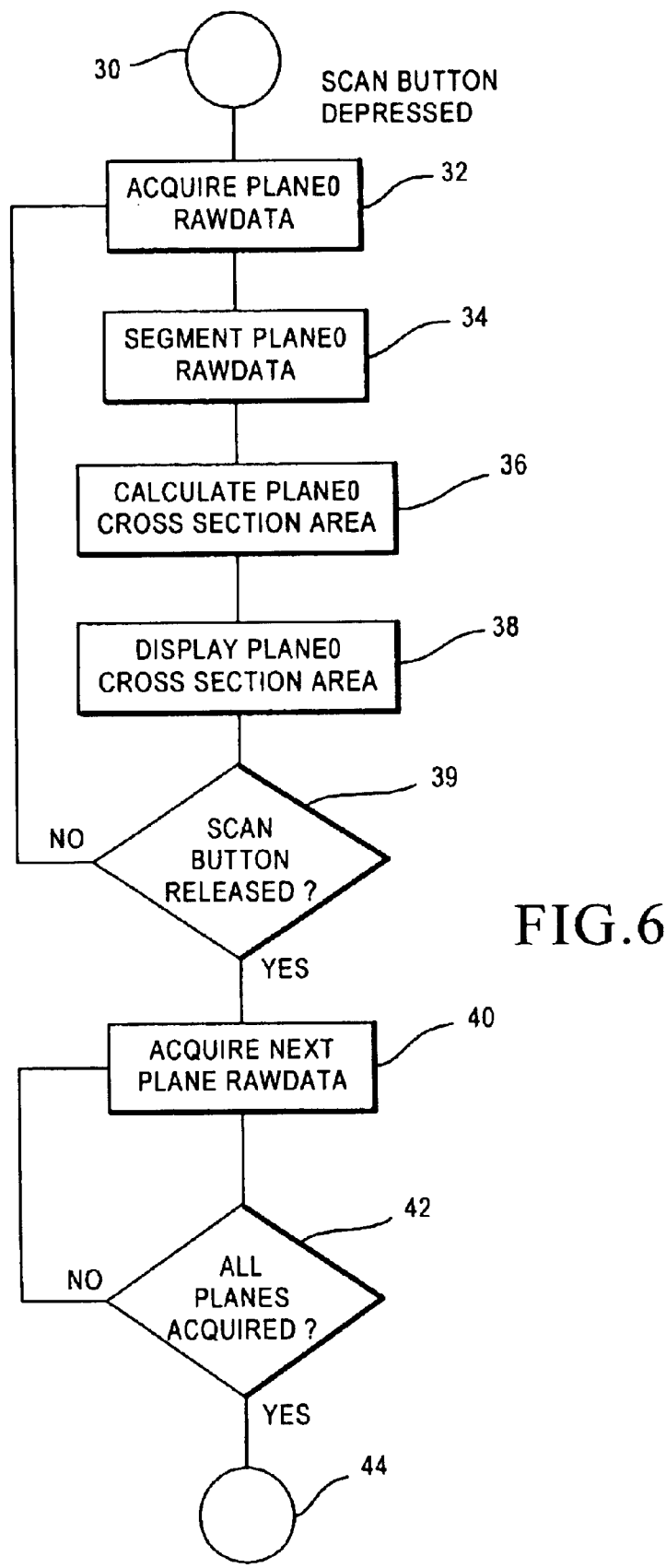
FIG. 6 is a software flowchart for operation of a second embodiment of the present invention.

A flowchart illustrating the above process in a sequence of steps is shown in FIG. 6. In a first step, shown at 30, a scan button on the device is depressed by the operator. Data is then acquired for a selected single ultrasound-scanning plane; the resulting raw data is segmented, at steps 32 and 34, respectively. The cross-sectional area of the bladder from the segmented information is then calculated at 36 and the cross-section is then displayed at 38.

The scan button is then interrogated to determine whether it has been released. If it has not been released, then the above steps in the program are repeated (block 39). This loop-back process continues until a maximum cross-section is determined, at which point the scan button is released. The transducer is held steady and the next scan plane, i.e. the next theta plane of raw data, at step 40 is acquired. The acquiring of information then continues in conventional fashion with the transducer moving in both the phi and theta directions, until all of the scan line information, i.e. all of the planes of data, has been acquired, as indicated at step 42. At that point, after all the planes of data have been acquired, the program terminates (block 44). Then, conventionally, the bladder volume is calculated and displayed.

A third system/method is faster even than the second embodiment, combining the "aiming arrow" approach of the first embodiment, but based on significantly less data than the first embodiment. A minimal amount of scan line information is used for the aiming function. This ensures that the aiming information is obtained and displayed quickly. One plane of data, such as used in the second embodiment, will represent typically anywhere from 1% to 10% of the data in a full three-dimensional scan, depending upon the number of scan planes comprising a full three-dimensional scan. The same total amount of data is acquired in this embodiment, but is spread throughout the cone instead of along a single plane. For instance, every tenth scan line can be collected, or alternatively, just the information in the vicinity of the outer cone ring is collected. Then, a determination is made as to whether there are any cone violations relative to the outer cone ring, with the appropriate aiming arrow being lit for aiming correction if there has been any cone violation.

In this third embodiment, a display is not needed and the processing is quite simple and fast. Movement of the transducer in response to a lit arrow will quickly produce an updated aiming determination. When no arrows are lit the transducer is properly aimed.

Accordingly, the invention comprises several embodiments of a system and corresponding method for initially aiming, i.e. orienting, an ultrasonic bladder instrument transducer on the body of a patient so as to obtain accurate ultrasonic information concerning the bladder.

It should be understood that, although the application uses the specific example of a bladder instrument, other human organs could be examined using the disclosed aiming methods.

Further, it should be understood that the aiming display disclosed herein could be directly on the scanning device itself. The directions to move the scanhead thus are on the scanhead itself, reducing possible confusion.

Although a preferred embodiment of the invention has been described for purposes of illustration, it should be understood that various changes, modification and substitutions might be incorporated in the embodiment without departing from the spirit of the invention, which is defined in the claims, which follow.

What is claimed:

1. A system for aiming a transducer portion of an ultrasonic bladder instrument in order to capture an image of a human organ, comprising:
   a function for generating a plurality of ultrasound scan planes, each separated by a selected angle, to produce a scan cone having an ultrasound scan cone boundary for scanning a human organ;
   a function for determining the amount, if any, of the scanned organ which extends beyond the cone boundary, defining a cone violation;
   a function for determining the extent to which the organ is centered within the ultrasound cone boundary when a cone violation is determined; and
   a display indicating that re-aiming of the ultrasound transducer is necessary when there is a cone violation and the organ is not centered by a selected amount.

2. The system of claim 1, wherein the function for determining the extent of centering includes determining the percentage of the organ within an inner cone boundary relative to that within the ultrasound cone boundary, wherein the inner cone boundary is inside the ultrasound cone boundary, and wherein re-aiming of the transducer is necessary when the organ percentage is less than a preselected number.

3. The system of claim 2, wherein the preselected number is approximately 70%.

4. The system of claim 1, wherein the human organ is a bladder.

5. The system of claim 1, wherein the signal display is in the form of lighting one of four orthogonal directional arrows, wherein the directional arrow which is lit indicates the appropriate direction of movement of the transducer on the patient for improving centering of the bladder within the ultrasound scan cone boundary.

6. The system of claim 5, wherein a directional arrow is lit in one state when re-aiming of the transducer is necessary and in a second state when re-aiming is optional.

7. The system of claim 6, wherein the one state is a blinking light and the second state is a solid light.

8. The system of claim 1, wherein said percentage is determined using the number of scan planes within the inner cone boundary and the number of scan lines within the ultrasound scan cone boundary.

9. The system of claim 1, wherein the amount of bladder extending beyond the ultrasound cone boundary is determined by the distance between the front wall and back wall of the bladder at the ultrasound cone boundary.

10. A system for aiming a transducer portion of an ultrasonic instrument image in order to accurately capture the image of a human organ, comprising:
    a function for generating a single ultrasound scan plane, wherein generation of the single scan plane is controlled by operation of a transducer control element;
    a display showing a cross-section of the organ determined from information from the single ultrasound scan plane when the transducer is initially placed on the patient's abdomen; and
    a function for implementing a three-dimensional ultrasound scan following termination of generation of the single ultrasound scan plane, when the cross-section of the organ on the display reaches a desired size by manipulating the position of the transducer on the patient, indicating desired aiming of the transducer.

11. The system of claim 10, wherein the human organ is the bladder.

12. The system of claim 11, wherein the control element is a switch, which is operated during aiming of the transducer and released when aiming is complete and the three-dimensional scan is to be initiated.

13. The system of claim 11, wherein the single ultrasound scan plane is generated continuously as long as the control element is operated.

14. The system of claim 11, wherein the desired size is a maximum cross-section of the bladder.

15. A system for aiming a transducer portion of an ultrasonic instrument in order to capture the image of a human organ, comprising:

a function for generating a plurality of ultrasound scan planes, producing ultrasound information concerning the organ, wherein the ultrasound information is within the range of 1%–10% of the ultrasound information for a full ultrasound image of the organ, wherein the scan planes are arranged in a cone configuration;

a function for determining whether the scanned organ image extends beyond a cone configuration produced by said ultrasound scan lines; and a signal indicating that re-aiming is necessary if the organ image is beyond the cone configuration.

16. The system of claim 15, wherein the organ is a bladder.

17. The system of claim 15, including a set of orthogonal directional arrows, wherein the signal produces an illumination of one of the arrows if re-aiming is necessary, indicating direction of movement of the transducer to correctly orient the apparatus.

18. A method for aiming a transducer portion of an ultrasonic bladder instrument in order to capture an image of a human organ, comprising the steps of:

generating a plurality of ultrasound scan planes, each separated by a selected angle, to produce a scan cone having an ultrasound scan cone boundary for scanning a human organ;

determining the amount, if any, of the scanned organ which extends beyond the cone boundary, defining a cone violation;

determining the extent to which the organ is centered within the ultrasound cone boundary when a cone violation is determined; and providing a display indicating that re-aiming of the ultrasound transducer is necessary when there is a cone violation and the organ is not centered by a selected amount.

19. The method of claim 18, wherein the function for determining the extent of centering includes determining the percentage of the organ within an inner cone boundary relative to that within the ultrasound cone boundary, wherein the inner cone boundary is inside the ultrasound cone boundary, and wherein re-aiming of the transducer is necessary when the bladder percentage is less than a preselected number.

20. The method of claim 19, wherein the preselected number is approximately 70%.

21. The method of claim 18, wherein the human organ is a bladder.

22. A method for aiming a transducer portion of an ultrasonic instrument image in order to accurately capture the image of a human organ, comprising the steps of:

generating a single ultrasound scan plane, wherein generation of the single scan plane is controlled by operation of a transducer control element;

providing a display showing a cross-section of the bladder determined from information from the single ultrasound scan plane when the transducer is initially placed on the patient's abdomen; and implementing a three-dimensional ultrasound scan following termination of generation of the single ultrasound scan plane, when the cross-section of the organ on the display reaches a desired size by manipulating the position of the transducer on the patient, indicating desired aiming of the transducer.

23. The method of claim 22, wherein the human organ is the bladder.

24. A method for aiming a transducer portion of an ultrasonic instrument in order to capture the image of a human organ, comprising the steps of:

generating a plurality of ultrasound scan planes, producing ultrasound information concerning the organ, wherein the ultrasound information is within the range of 1%–10% of the ultrasound information for a full ultrasound image of the organ, wherein the scan planes are arranged in a cone configuration;

determining whether the scanned organ image extends beyond a cone configuration produced by said ultrasound scan lines; and providing a signal indicating that re-aiming is necessary if the organ image is beyond the cone configuration.

25. The method of claim 24, wherein the organ is a bladder.

* * * * *